United States Patent
Heimbrock et al.

(10) Patent No.: US 8,125,318 B2
(45) Date of Patent: Feb. 28, 2012

(54) WIRELESS CONTROL SYSTEM FOR A PATIENT-SUPPORT APPARATUS

(75) Inventors: Richard H. Heimbrock, Cincinnati, OH (US); Craig A. McNeely, Columbus, IN (US); Keith A. Huster, Sunman, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 1027 days.

(21) Appl. No.: 11/216,296

(22) Filed: Aug. 31, 2005

(65) Prior Publication Data
US 2006/0058587 A1  Mar. 16, 2006

Related U.S. Application Data

(60) Provisional application No. 60/608,980, filed on Sep. 10, 2004.

(51) Int. Cl.
*A61N 1/08* (2006.01)

(52) U.S. Cl. ............. 340/12.22; 600/300; 340/4.11

(58) Field of Classification Search ............ 340/825.69, 340/5.8, 286.07, 10.3, 825.22, 4.11, 4.3, 340/12.22, 12.23, 12.24, 12.5, 12.51; 600/300
See application file for complete search history.

(56) References Cited

U.S. PATENT DOCUMENTS

| | | | |
|---|---|---|---|
| 3,137,773 A | 6/1964 | Black | |
| 3,644,946 A | 2/1972 | Swatt | |
| 3,711,664 A | 1/1973 | Benoit et al. | |
| 3,716,876 A | 2/1973 | Petzon et al. | |
| 3,781,927 A | 1/1974 | Zakaras | |
| 3,846,857 A | 11/1974 | Weinstock | |
| 3,865,430 A | 2/1975 | Tanus | |
| 3,872,526 A | 3/1975 | Betts | |
| 3,913,153 A | 10/1975 | Adams et al. | |
| 3,923,300 A | 12/1975 | Tanus | |
| 3,932,903 A | 1/1976 | Adams et al. | |
| 3,972,081 A | 8/1976 | Stern et al. | |
| 4,014,344 A | 3/1977 | Gutierrez | |
| 4,044,286 A | 8/1977 | Adams et al. | |
| 4,062,075 A | 12/1977 | Stern et al. | |
| 4,211,998 A | 7/1980 | Junginger et al. | |
| 4,218,681 A | 8/1980 | Hörmann | |
| 4,231,109 A | 10/1980 | Junginger et al. | |
| 4,232,901 A | 11/1980 | Harrington et al. | |
| 4,294,048 A | 10/1981 | Sutter | |
| 4,371,815 A | 2/1983 | Jones, Jr. et al. | |
| 4,435,862 A | 3/1984 | King et al. | |
| 4,639,959 A | 2/1987 | Roca | |
| 4,680,790 A | 7/1987 | Packard et al. | |

(Continued)

FOREIGN PATENT DOCUMENTS

CH          675936 A5    11/1990

(Continued)

*Primary Examiner* — Nabil Syed
(74) *Attorney, Agent, or Firm* — Barnes & Thornburg LLP

(57) ABSTRACT

A wireless control system for use with a patient-support apparatus includes a first receiver located on the patient-support apparatus and a wireless hand-held controller configured to wirelessly communicate with the first receiver to control functions of the patient-support apparatus and/or functions of hospital room equipment. The wireless control system may also include a second receiver located apart from the patient-support apparatus. The wireless hand-held controller may be configured to wirelessly communicate with the second receiver to control functions of the hospital room equipment. Additionally, the wireless control system may include a docking station configured to receive and charge the wireless hand-held controller.

11 Claims, 5 Drawing Sheets

U.S. PATENT DOCUMENTS

| | | | |
|---|---|---|---|
| 4,712,105 A | 12/1987 | Köhler | |
| 4,728,949 A * | 3/1988 | Platte et al. | 340/825.37 |
| 4,745,647 A | 5/1988 | Goodwin | |
| 4,769,584 A | 9/1988 | Irigoyen et al. | |
| 4,787,104 A | 11/1988 | Grantham | |
| 4,798,197 A | 1/1989 | Nippoldt et al. | |
| 4,825,200 A | 4/1989 | Evans et al. | |
| 4,850,040 A | 7/1989 | Teich et al. | |
| 4,916,441 A | 4/1990 | Gombrich | |
| 4,955,000 A | 9/1990 | Nastrom | |
| 4,967,195 A | 10/1990 | Shipley | |
| 4,992,784 A * | 2/1991 | Ruttiger | 340/825.72 |
| 4,999,622 A | 3/1991 | Amano et al. | |
| 5,044,029 A | 9/1991 | Vrzalik | |
| 5,053,636 A | 10/1991 | Zelina | |
| 5,057,932 A | 10/1991 | Lang | |
| 5,058,871 A | 10/1991 | Congin et al. | |
| 5,062,167 A | 11/1991 | Thomas et al. | |
| 5,063,623 A | 11/1991 | Bathrick et al. | |
| 5,063,624 A | 11/1991 | Smith et al. | |
| 5,072,463 A | 12/1991 | Willis | |
| 5,073,999 A | 12/1991 | Thomas et al. | |
| 5,098,089 A | 3/1992 | Harrington et al. | |
| 5,107,554 A | 4/1992 | Garakani | |
| 5,235,258 A | 8/1993 | Schuerch | |
| 5,239,300 A | 8/1993 | Berger et al. | |
| 5,437,608 A | 8/1995 | Cutler | |
| 5,452,356 A | 9/1995 | Albert | |
| 5,481,255 A | 1/1996 | Albert et al. | |
| 5,509,154 A | 4/1996 | Shafer et al. | |
| 5,513,400 A | 5/1996 | Turner | |
| 5,540,651 A | 7/1996 | Risch et al. | |
| 5,542,138 A | 8/1996 | Williams et al. | |
| 5,544,376 A | 8/1996 | Fromson | |
| 5,561,412 A | 10/1996 | Novak et al. | |
| 5,600,214 A | 2/1997 | Fromson | |
| 5,600,311 A * | 2/1997 | Rice et al. | 340/4.11 |
| 5,611,096 A | 3/1997 | Bartlett et al. | |
| 5,627,531 A | 5/1997 | Posso et al. | |
| 5,627,584 A | 5/1997 | Nishikori et al. | |
| 5,652,484 A | 7/1997 | Shafer et al. | |
| 5,678,568 A | 10/1997 | Uchikubo et al. | |
| 5,682,631 A | 11/1997 | Weismiller et al. | |
| 5,699,038 A | 12/1997 | Ulrich et al. | |
| 5,735,285 A | 4/1998 | Albert et al. | |
| 5,737,781 A | 4/1998 | Votel | |
| 5,745,937 A | 5/1998 | Weismiller et al. | |
| 5,754,997 A | 5/1998 | Lüssi et al. | |
| 5,771,511 A | 6/1998 | Kummer et al. | |
| 5,838,223 A | 11/1998 | Gallant et al. | |
| 5,848,450 A | 12/1998 | Oexman et al. | |
| 5,890,238 A | 4/1999 | Votel | |
| 5,926,002 A | 7/1999 | Cavanaugh et al. | |
| 5,969,488 A | 10/1999 | Fromson | |
| 6,008,598 A | 12/1999 | Luff et al. | |
| 6,035,465 A | 3/2000 | Rogozinski | |
| 6,037,723 A | 3/2000 | Shafer et al. | |
| 6,048,310 A | 4/2000 | Yasushi et al. | |
| 6,078,261 A | 6/2000 | Davsko | |
| 6,079,065 A | 6/2000 | Luff et al. | |
| 6,127,941 A | 10/2000 | Van Ryzin | |
| 6,131,868 A | 10/2000 | Welling et al. | |
| 6,135,949 A | 10/2000 | Russo et al. | |
| 6,341,393 B1 | 1/2002 | Votel | |
| 6,351,678 B1 | 2/2002 | Borders | |
| 6,378,148 B1 | 4/2002 | Votel | |
| 6,396,224 B1 | 5/2002 | Luff et al. | |
| 6,560,492 B2 | 5/2003 | Borders | |
| 6,570,491 B1 | 5/2003 | Bastholm | |
| 6,753,790 B2 * | 6/2004 | Davies et al. | 340/825.69 |
| 6,772,456 B2 | 8/2004 | Votel | |
| 7,068,143 B2 | 6/2006 | Doering et al. | |
| 2002/0014951 A1 | 2/2002 | Kramer et al. | |
| 2004/0207535 A1 * | 10/2004 | Stevenson et al. | 340/825.22 |

FOREIGN PATENT DOCUMENTS

| | | |
|---|---|---|
| DE | 26 30 334 | 12/1978 |
| DE | 31 19 876 A1 | 12/1982 |
| DE | 31 09 166 A1 | 1/1983 |
| EP | 0 178 951 A2 | 4/1986 |
| EP | 0 220 708 A2 | 5/1987 |
| EP | 0 228 233 A2 | 7/1987 |
| EP | 0 261 830 A2 | 3/1988 |
| EP | 0 302 579 A1 | 2/1989 |
| EP | 0 316 643 A2 | 5/1989 |
| EP | 0 341 358 A1 | 11/1989 |
| EP | 0 341 570 A2 | 11/1989 |
| EP | 0 348 726 S2 | 1/1990 |
| EP | 0 373 912 A2 | 6/1990 |
| EP | 0 453 363 A1 | 10/1991 |
| EP | 0 455 852 A1 | 11/1991 |
| EP | 0 488 552 A2 | 6/1992 |
| EP | 0 505 312 A1 | 9/1992 |
| EP | 0 505 847 A1 | 9/1992 |
| EP | 0 999 533 A2 | 5/2000 |
| GB | 1 404 038 | 8/1975 |
| GB | 2 210 554 A | 6/1989 |
| JP | 50-95978 | 7/1975 |
| JP | 54-45472 | 4/1979 |
| JP | 54-45473 | 4/1979 |
| JP | 59-186009 | 10/1984 |
| JP | 4-322611 | 11/1992 |
| JP | 10-337314 | 12/1998 |
| JP | 2001-494 | 1/2001 |
| NL | 8902202 | 3/1991 |
| WO | WO 90/06739 | 6/1990 |
| WO | WO 99/23990 | 5/1999 |
| WO | WO 99/52487 | 10/1999 |

\* cited by examiner

US 8,125,318 B2

WIRELESS CONTROL SYSTEM FOR A PATIENT-SUPPORT APPARATUS

This patent application claims priority to and the benefit of U.S. Provisional Patent Application Ser. No. 60/608,980 entitled "Wireless Control System for a Patient-Support Apparatus" which was filed on Sep. 10, 2004, the entirety of which is expressly incorporated herein by reference.

BACKGROUND OF THE INVENTION

The present disclosure relates generally to wireless control systems for patient-support apparatuses, such as hospital beds. More particularly, the present disclosure relates to wireless control systems having a wireless controller usable by a patient or other person to control functions of the patient-support apparatus and/or other hospital room equipment.

Typical hospital beds have a number of patient input devices, such as buttons, for controlling functions of the bed and other hospital room equipment such as entertainment devices, environment control devices, and/or a nurse call system. The patient input devices are typically located on one or more siderails of the bed. However, some patients may have difficulty in identifying and/or accessing the patient input devices that are located on the siderails of the bed. For example, a patient may have difficulty accessing the patient input devices from a resting position on the bed. Additionally, the patient may have difficulty accessing and/or identifying the patient input devices such as when the patient is standing next to the bed or sitting in a nearby chair. Some hospital beds may include a wired or otherwise tethered pendant or controller having a selection of patient input devices located thereon. However, the wires of the pendant may become entangled with other lines, such as IV lines, patient monitoring lines, catheter lines, nasogastric lines, and the like.

SUMMARY OF THE INVENTION

The present invention comprises one or more of the features recited in the appended claims and/or the following features which, alone or in any combination, may comprise patentable subject matter:

A wireless control system for use with a patient-support apparatus is provided. The wireless control system may include a first receiver located on a siderail of the patient-support apparatus. The first receiver may be a portion of a transceiver. The wireless control system may also include a second receiver located away from the patient-support apparatus. The second receiver may be located in a wall of a hospital and may form a portion of a nurse call system. Alternatively, the second receiver may form a portion of a hospital room device or equipment such as a television, radio, light, temperature control system, and the like. The first and/or second receivers may be infrared receivers. The wireless control system may further include a wireless hand-held controller. The wireless hand-held controller may be configured to communicate with the first receiver to control functions of the patient-support apparatus. Additionally, the wireless hand-held controller may be configured to communicate with the second receiver to control functions of hospital room equipment. The wireless hand-held controller may communicate with the first and/or second receivers using one or more wireless communication technologies such as infrared and/or radio frequency and using a suitable communication protocol such as Bluetooth, Zigbee, Wireless Fidelity, and/or one or more of Infrared Data Association's protocols. The wireless hand-held controller may be configured to communicate with the first receiver only within a distance of the patient-support apparatus and/or only within a predetermined distance of a patient identification wristband. The wireless hand-held controller may also be configured to be received by a docking station located on the patient-support apparatus. The docking station may charge the wireless hand-held controller, such as via inductive charging, while the wireless hand-held controller is positioned in the docking station. The wireless control system may further include another receiver located on the patient-support apparatus and facing away from a mattress of the patient-support apparatus.

A patient-support apparatus is also provided. The patient-support apparatus may include a frame. The frame may have a patient-occupancy region for supporting the patient. The patient-support apparatus may also include a first wireless receiver coupled to the frame. The first wireless receiver may be positioned to face generally toward the patient-occupancy region. The patient-support apparatus may also include a second wireless receiver coupled to the frame. The second wireless receiver may be positioned to face generally away from the patient-occupancy region. The frame may also include a siderail to which the first and second wireless receivers are coupled. The first and second wireless receivers may be infrared and/or radio frequency receivers and may be configured to receive wireless communications from a wireless hand-held controller. Such wireless communications may use a communication protocol such as Bluetooth, Zibgee, Wireless Fidelity, and one or more of Infrared Data Association's protocols. The wireless communications may include control signals for controlling functions of the patient-support apparatus. The patient-support apparatus may also include a transmitter configured to communicate with a nurse call system and/or a docking station configured to receive and charge the wireless hand-held controller.

Alternatively, the patient-support apparatus may include a frame, a deck coupled to the frame, a siderail coupled to the frame, and a docking station located on the siderail. The patient-support apparatus may also include a wireless hand-held controller for use by a patient to control the elevation of a section of the deck. The docking station may be configured to receive the wireless hand-held controller. The docking station may charge, for example inductively charge, the wireless hand-held controller while so received. The wireless hand-held controller may be used by the patient to also control functions of hospital room equipment such as entertainment devices and/or environment control devices.

Additionally, a wireless hospital bed control system is provided. The wireless hospital bed control system may include a wireless hand-held controller. The wireless hand-held controller may be able to communicate with a plurality of hospital beds, but may be programmable by a caregiver to communicate with only one, designated hospital bed of the plurality of beds. The wireless hand-held controller may also be programmable to communicate with hospital room equipment to control functions of the equipment. The wireless hand-held controller may have a limited communication range with the designated bed, such as less than about twenty-four inches. Additionally, the wireless hand-held controller may be capable of controlling functions of the bed only within a predetermined distance from a patient identification band, such as a wristband. The wireless hand-held controller may include a program button selectable by a patient or other person to program the controller to communicate with the designated bed. The wireless hand-held controller may have a programming range relative to the bed that is less than the communication range. For example, the programming range may be less than about six inches. The wireless hand-held controller may also include a visual indicator for providing a visual indication that the controller has been programmed to communicate with the designated bed.

The above and other features of the present disclosure, which alone or in any combination may comprise patentable subject matter, will become apparent from the following description and the attached drawings.

BRIEF DESCRIPTION OF THE DRAWINGS

The detailed description particularly refers to the following figures, in which.

DETAILED DESCRIPTION OF THE DRAWINGS

Figure 1:
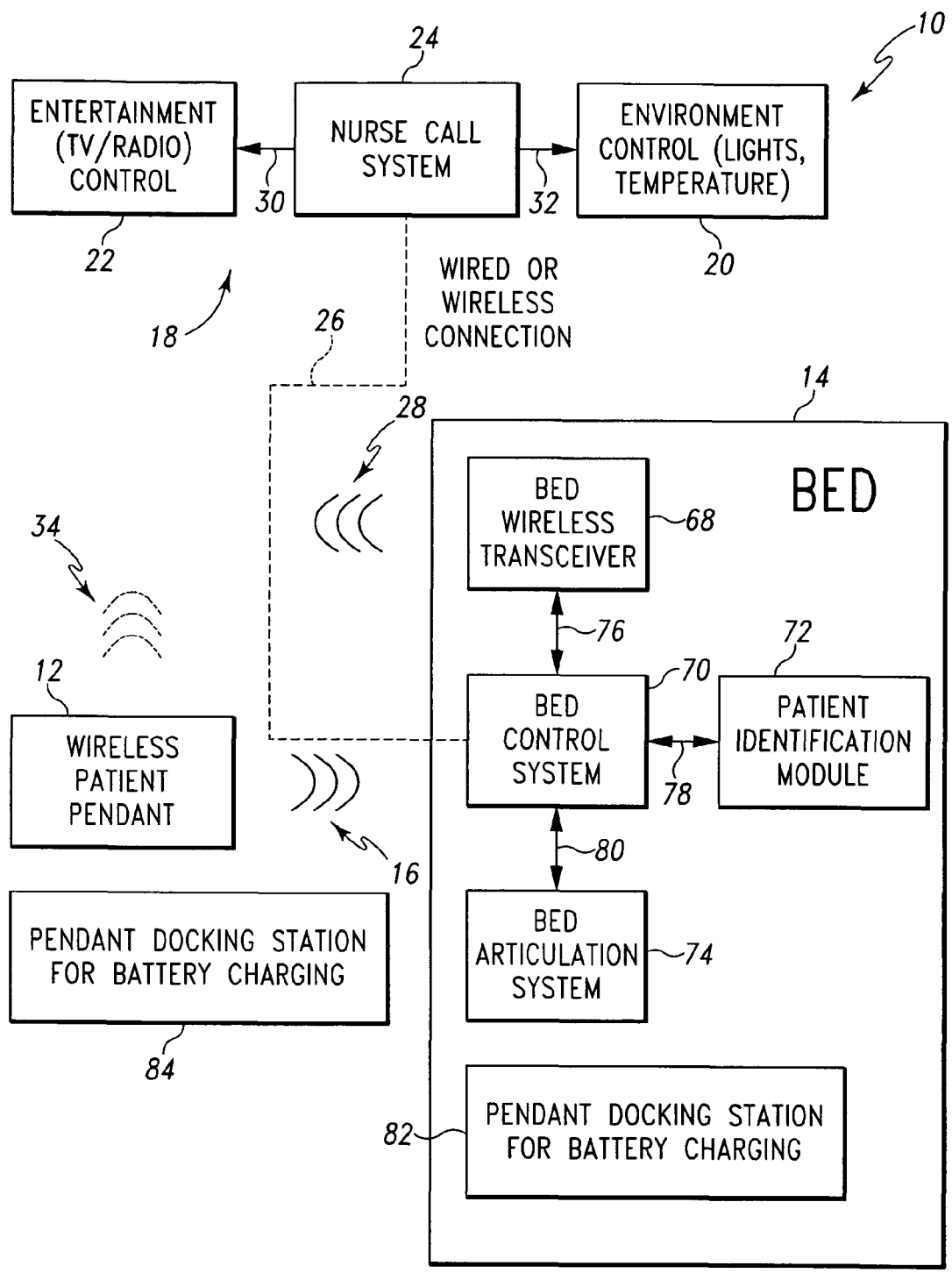
FIG. 1 is a block diagram of a wireless control system having a wireless patient pendant that controls functions of a bed and equipment spaced from the bed.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

Referring to FIG. 1, a wireless control system 10 includes a wireless hand-held controller or patient pendant 12 and a patient-support apparatus 14. The apparatus 14 may be, for example, a hospital bed, hospital stretcher, hospital chair, or any other device used to support a patient. The controller 12 is configured to communicate with the apparatus 14 using wireless communication as illustrated in FIG. 1 by wireless communication signals 16. The controller 12 may use any wireless communication technology to communicate with the apparatus 14 including, but not limited to, radio frequency (RF) technology and infrared (IR) technology. Additionally, the controller 12 may use any wireless communication protocol to communicate with the apparatus 14. For example, the controller 12 may use an RF communication protocol such as Bluetooth, Zigbee, Wireless Fidelity (WiFi), or any other type of RF communication protocol. Alternatively, the controller 12 may use an IR communication protocol such as one or more of the Infrared Data Association's (IrDA) protocols or any other type of IR communication protocol.

The controller 12 is usable by a patient to wirelessly control functions of the apparatus 14. For example, a patient may use the controller 12 to articulate sections of the apparatus 14 such as elevating a head section of the apparatus 14, turn on/off lights associated with the apparatus 14, or any other function of the apparatus 14 typically controllable by a patient (for example, via a patient input button located on the apparatus 14).

In some embodiments, the controller 12 is also configured to wirelessly control functions of hospital room equipment 18. For example, the controller 12 may be configured to wirelessly control functions of environment control devices 20 such as room lights and/or thermostats, entertainment devices 22 such as televisions and/or radios, a nurse calls system 24, or any other equipment located in or associated with a hospital room including any equipment commonly controllable via patient input buttons located on the apparatus 14. Such functions may include on/off, volume up/down, silent on/off, nurse call, and/or any other function based on the particular type of hospital room equipment 18. Additionally, the equipment 18 may include a network (not shown) such as a local area network (LAN), a wide area network (WAN), or any other type of network. The system 24 may form a portion of the network or may otherwise be coupled to the network.

In some embodiments, the controller 12 is configured to control the hospital room equipment 18 by wirelessly communicating one or more control signals to the apparatus 14. In response, the apparatus 14 is configured to relay or otherwise communicate control signals to the equipment 18 based on the controls signals received from the controller 12. The apparatus 14 may communicate the control signals via wired or wireless communication. For example, as illustrated in FIG. 1, the apparatus 14 may communicate the control signals via a wired connection 26. The wired connection 26 may be embodied as any number of wires, optic fibers, or other interconnection devices. Alternatively, the apparatus 14 may communicate the control signals via wireless communication as illustrated in FIG. 1 by wireless communication signals 28. In some embodiments, the apparatus 14 may communicate the control signals through the network (not shown) and/or the nurse call system 24. If the control signals are nurse call control signals such as a nurse call request, the system 24 responds to the control signals by, for example, alerting a nurse associated with the patient. However, if the control signals are entertainment control signals or environment control signals, the nurse call system 24 communicates such signals to the appropriate entertainment device 22 or environment control device 20 via communication links 30, 32, respectively. The communication links 30, 32 may be any type of communication links including, but not limited to, wired communication links such as wires, fiber optic cables, and/or other electrical interconnects or wireless communication links such as RF and/or IR communication links. Alternatively, the apparatus 14 may communicate the control signals directly to the entertainment device 22, the environment control device 20, or the nurse call system 24 based on the type of the control signal. For example, if the control signal is an entertainment device control signal, the apparatus 14 may communicate the control signal to the entertainment device 22 via wireless communication as illustrated by wireless communication signals 28.

In an alternative embodiment, the controller 12 may be configured to communicate directly with one or more of the hospital room equipment devices 18. In such embodiments, the controller 12 communicates wirelessly with the hospital room equipment 18 as illustrated in FIG. 1 via wireless communication signals 34. For example, the controller 12 may be configured to control an entertainment device 22, such as a television or radio, via wireless communication. Any hospital room equipment 18 that is wirelessly controllable by the controller 12 includes an appropriate receiver configured to receive the wireless communication signals 34 from the controller 12. The controller 12 may use any wireless communication technology to communicate with the hospital room equipment 18 including, but not limited to, RF and IR technology using any appropriate communication protocol such as Bluetooth, Zigbee, Wireless Fidelity (WiFi), one or more Infrared Data Association's (IrDA) protocols, or any other type of RF and/or IR communication protocol. For example, the controller 12 may use a first type of wireless communication technology and/or protocol to communicate with the apparatus 14 and a second type of wireless communication technology and/or protocol to communicate with the hospital room equipment 18. Accordingly, in such embodiments, the controller 12 wirelessly communicates with the apparatus 14 to control functions of the apparatus 14 as illustrated by wireless communication signals 16 and wirelessly communicates with one or more hospital room equipment devices 18 (e.g., entertainment device 22, environment control device 20, and/or nurse call system 24) to control functions of the one or more devices 18 as illustrated by wireless communication signals 34. In one particular embodiment, the controller 12 is configured to communicate with the apparatus 14 to control functions of the apparatus 14 and functions of the nurse call system 24 and communicate directly with one or more entertainment control device 22 and/or environment control device 20.

Figure 2:
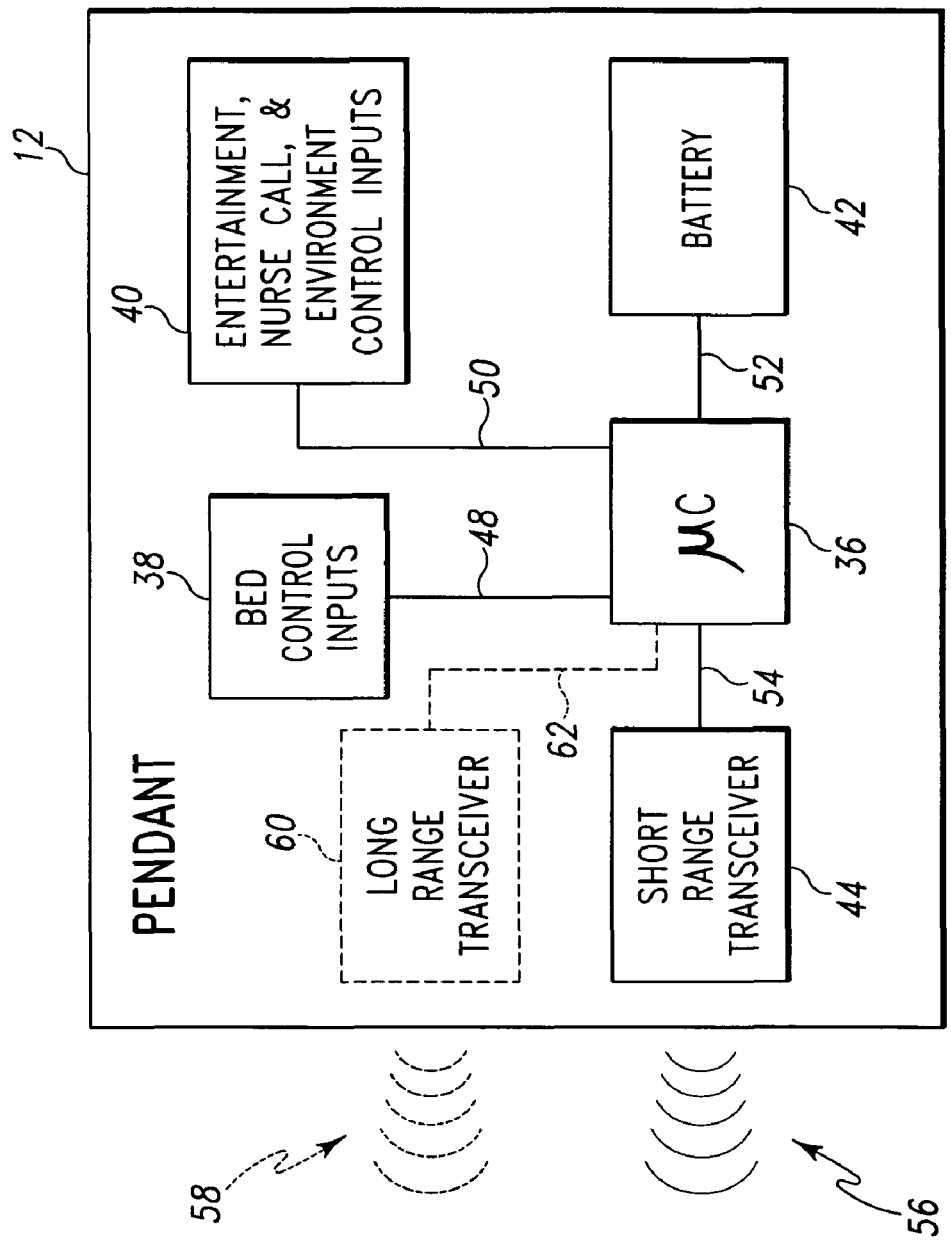
FIG. 2 is a block diagram of the wireless pendant of the wireless control system of FIG. 1.

Referring now to FIG. 2, an illustrative controller 12 for use by a patient includes a microprocessor 36, a number of patient-support control inputs 38, a number of hospital room equipment control inputs 40, a battery 42, and a transmitter or transceiver 44. As used herein, the term "transmitter" is intended to refer to any device capable of transmitting wireless communication signals including, but not limited to, dedicated wireless transmitters, wireless transceivers, and the like. The controller 12 may also include other components typically included in a wireless controller. For example, the controller 12 may also include a memory device, a display, display driver circuitry, visual indicators such as light emitting diodes (LEDs), audible indicators such as piezoelectric speakers, or any other type of electrical component. Additionally, although in FIG. 2 the components of the controller 12 are illustrated as separate components, in some embodiments, one or more of the components may be embodied as a single component. For example, in some embodiments, the transmitter 44 may be included in the microprocessor 36.

The control inputs 38, 40, battery 42, and transmitter 44 are coupled to and communicate with the microprocessor 32 via signal paths 48, 50, 52, 54, respectively. The signal paths 48, 50, 52, 54 may be any type of signal paths capable of providing communication between the components including, but not limited to, wires, printed circuit board (PCB) traces, and/or vias. The microprocessor 36 may be embodied as any type of microprocessor including, but not limited to, a general microprocessor, a dedicated microprocessor having software/firmware embedded therein, a microcontroller, a collection of low level devices such as logic gates, or any other type of processing unit(s).

The patient-support control inputs 38 and hospital room equipment control inputs 40 may be embodied as any type of patient input device such as buttons, switches of all types, knobs, dials, touch screens, levers, voice-activated sensors, associated software switches, and the like. Accordingly, as used herein, the term "control input" is intended to mean devices of any and all types that may be interacted with by the patient to provide some sort of signal (e.g., an input or control signal). The patient-support control inputs 38 may include any number of control inputs selectable by the patient to control functions of the apparatus 14. For example, the control inputs 38 may include control inputs for articulating the apparatus 14 such as elevating a head section or a foot section of the apparatus 14. In one specific embodiment, the patient-support control inputs 38 include a number of control inputs corresponding to a number of patient control inputs (not shown) located on the apparatus 14.

Similarly, the hospital room equipment control inputs 40 may include any number of control inputs selectable by the patient to control functions of one or more hospital room equipment devices 18 such as environment control devices 20, entertainment device 22, and/or nurse call system 24. For example, the control inputs 40 may include control inputs for controlling functions of a television or radio such as on/off control, volume adjustment, tuning, and/or silencing. Additionally, the control inputs 40 may include control inputs for controlling functions such as on/off control and/or other adjustments of a hospital room light, nightlight, thermostat, or the like. Further, the control inputs 40 may include control inputs for controlling functions of the nurse call system 24 such as requesting the service of a nurse associated with the patient. It should be understood that the control inputs 38 may include a control input for performing any function of a hospital room equipment device 18 having a receiver configured to receive wireless communications from the controller 12. Additionally, in some embodiments, a single control input 40 may be configurable, e.g. by selecting an equipment selection input (not shown), to control functions of multiple hospital room equipment devices 18. For example, a single control input 40 may be selectable by the patient to control the volume of a television or control the volume of a radio by first selecting the appropriate equipment selection input.

The battery 42 may be any type of battery including an alkaline battery, lithium battery, nickel cadmium battery, or the like. Additionally the battery 42 may be comprised of any number of batteries configured in a series or parallel configuration to provide one of a range of voltage and current capabilities. In one particular embodiment, the battery 42 is a rechargeable battery. The controller 12 may also include charging contacts (not shown) on the outside of the controller 12 for charging the battery 42. In such embodiments, the charging contacts are electrically coupled to the battery 42. Alternatively, the wireless controller 12 may include a rechargeable battery 42 but not include charging contacts. In such embodiments, the battery 42 may be charged by alternative charging methods that do not require physical connection to the battery (e.g., inductive charging).

The transmitter may be any type of transmitter including an RF or IR transmitter. The transmitter 44 and microprocessor 36 may be configured to use any type of wireless communication protocol including Bluetooth, Zigbee, Wireless Fidelity (WiFi), one or more of the Infrared Data Association's (IrDA) protocol, or any other type of RF and/or IR communication protocol. In one embodiment, the transmitter 44 is configured to wirelessly communicate with the apparatus 14 and with one or more hospital room equipment devices 18 via wireless communication signals 56. However, in a particular alternative embodiment, the transmitter 44 may be configured to communicate only with the apparatus 14. In such embodiments, the transmitter 44 may be a short range transmitter having a communication range of about twenty-four inches or less. Such a short range transmitter communicates with the apparatus 14 only within the short communication range. A controller 12 having a short range transmitter reduces the possibility that the patient may inadvertently control the wrong patient-support apparatus or inadvertently control more than one patient-support apparatus at a time. In embodiments in which the transmitter 44 is a short range transmitter, the controller 12 may also include a separate long range transmitter 60 for communicating with one or more hospital room equipment devices 18 via wireless communication signals 58. The transmitter 60 is electrically coupled to the microprocessor 36 via a signal path 62 such as a number of wires, PCB traces, or vias. The transmitter 60 may be configured to communicate with a single equipment device 18 or a number of equipment devices 18.

In an alternative embodiment, the controller 12 is programmable to communicate with only a single designated apparatus 14. In such embodiments, the transmitter 44 may or may not be a short range transmitter. The controller 12 may include one or more programming input devices (not shown), such as a programming button, for programming the controller 12 to the designated apparatus 14. Additionally, the controller 12 may include a visual indicator such as an LED to visually indicate that the controller 12 has been programmed to the designated apparatus 14. While so programmed, the controller 12 is operable to control only the designated apparatus 14 to the exclusion of other patient-support apparatuses located nearby. To reduce the possibility that the patient 66 or other person inadvertently re-programs the controller 12 to another apparatus 14, the programming input device may be operable only within a predetermined programming range of the apparatus 14. In one particular embodiment, the programming range is about six inches or less. While the controller 12 is within the programming range, the programming input device may be selected by a patient or caregiver to program or otherwise associate the controller 12 with the apparatus 14 used by the patient. Accordingly, the controller 12 and/or the apparatus 14 may include additional circuitry and other devices for determining if the controller 12 is within the programming range. For example, the controller 12 may include an additional transmitter having a communication range less than the transmitter 44. Alternatively, the apparatus 14 may include circuitry to determine if the controller 12 is within the programming range based on one or more data criteria such as signal strength.

The controller 12 may also include a programming input device for programming the controller 12 to one or more of the hospital room equipment devices 18. For example, the controller 12 may include a television programming button selectable by the patient or caregiver to program the controller 12 to the particular type, brand, and/or model of television, radio, or other entertainment and/or environment control device located in the hospital room. Accordingly, a hospital may retain a number of controllers 12, each controller 12 being programmable to control any one of a number of apparatuses 14 and any number of hospital room equipment devices 18.

Figure 3:
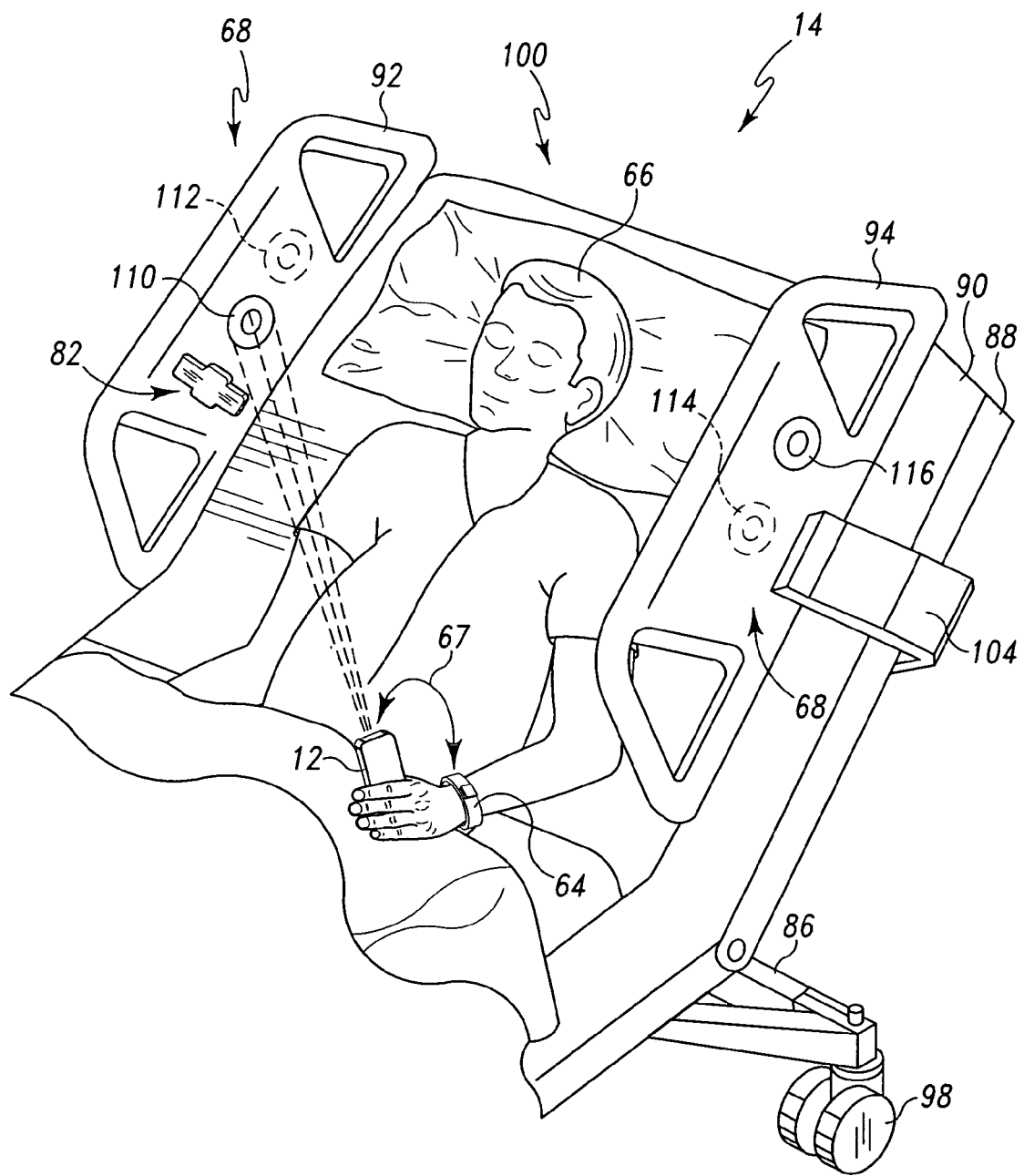
FIG. 3 is a perspective view, with portions broken away, showing a patient operating the wireless patient pendant of FIG. 2 to communicate with a first receiver located on a siderail of the bed.

In an additional alternative embodiment, the controller 12 may be configured to communicate with the apparatus 14 only while operated by a designated patient associated with the apparatus 14. For example, as illustrated in FIG. 3, the controller 12 may be configured to communicate with the apparatus 14 only while within a predetermined distance of a patient identification wristband 64 worn by a patient 66. In such embodiments, the controller 12 includes appropriate circuitry to determine if the controller 12 is within the predetermined distance from the wristband 64. For example, in some embodiments, the controller 12 may wirelessly communicate with the wristband 64 via wireless communication signals 67. Additionally, the wristband 64 may include circuitry or other devices for communicating with the controller 12. The controller 12 may be configured to communicate with the apparatus 14 only while within a predetermined distance of any patient identification wristband 64 or, alternatively, only while within a predetermined distance of a single, designated patient identification wristband 64. In the latter embodiments, the controller 12 may include one or more programming buttons selectable by the patient 66 or caregiver to program or otherwise associate the controller 12 with the designated wristband 64. While so programmed, the controller 12 is unusable by other patients to control the apparatus 14 associated with the patient 66.

Referring back to FIG. 1, the illustrative apparatus 14 includes one or more bed wireless receivers or transceivers 68. As used herein the term "receiver" is intended to refer to any device capable of receiving wireless communications including, but not limited to, dedicated wireless receivers, wireless transceivers, and the like. The receiver(s) 68 may be embodied as any type of receiver capable of communicating with the wireless controller 12 including RF or IR receivers. The receiver(s) 68 may be configured to receive any type of wireless communication protocol including Bluetooth, Zigbee, Wireless Fidelity (WiFi), one or more of the Infrared Data Association's (IrDA) protocols, or any other type of RF and/or IR communication protocol. In one particular embodiment, the receiver(s) 68 is configured to receive wireless communications from the controller 12 and transmit wireless communications to one or more hospital room equipment devices 18 such as the nurse call system 24, an entertainment device 22, and/or an environment control device 20 as illustrated by wireless communication signals 28.

The apparatus 14 also includes a bed control system 70, a patient identification module 72, and a bed articulation system 74. The receiver(s) 68, the patient identification module 72, and the bed articulation system 74 are electrically coupled to and communicate with the bed control system 70 via signal paths 76, 78, and 80, respectively. Although the signal paths 76, 78, 80 are illustrated as single interconnects, the paths 76, 78, 80 may include any number of interconnects. Additionally, the signal paths 76, 78, 80 may be embodied as any type of signal path including, but not limited to, wires, PCB traces, and wireless connections.

The bed control system 70 includes electronics, communication networks, and other devices for controlling functions of the apparatus 14 and for communicating with the receiver(s) 68, the module 72, and the system 74. The patient identification module 72 includes electronics, communication networks, and other devices configured to identify the patient associated with the apparatus 14 (e.g., the patient resting on the apparatus 14). The patient identification module 72 may identify the patient via any one of a number of patient identification technologies including, but not limited to, radio frequency identification (RFID), barcode scanning, electromagnetic identification, and the like. For example, the module 72 may include a RFID reader configured to interrogate or otherwise communicate with the patient identification wristband 64 worn by a patient and to determine the identify of the patient based thereon. The bed articulation system 74 includes electrical and mechanical components to facilitate the articulation functionality of the apparatus 14. For example the system 74 may include drive circuits, electro-mechanical actuators, hydraulic cylinders, electric motors, associated gears such as lead screws and worm gears, and linkages, as well as combinations of these elements.

The apparatus 14 includes a wireless hand-held controller or pendent docking station 82. However, in other embodiments, the apparatus 14 may not include any or may include any number of docking stations 82. The docking station 82 is configured to receive the controller 12. The patient 66 may position the controller 12 in the docking station 82 when the controller 12 is not in use by the patient 66. In some embodiments, the docking station 82 is configured to charge the controller 12 while the controller 12 is positioned in or otherwise received by the docking station 82. If the controller 12 includes charging contacts, the docking station 82 may include corresponding charging contacts positioned to contact the charging contacts of the controller 12 while controller 12 is positioned in the docking station 82. In an alterative embodiments, the docking station 82 is configured to inductively charge the controller 12 while the controller 12 is received by the station 82. In such embodiments, the docking station 82 may or may not include charging contacts. The wireless control system 10 may also include any number of other docking stations 84 located apart from the apparatus 14. For example, the wireless control system 10 may include a docking station 84 located at a nurse call center for charging a number of controllers 12 stored at the nurse call center.

Figure 4:
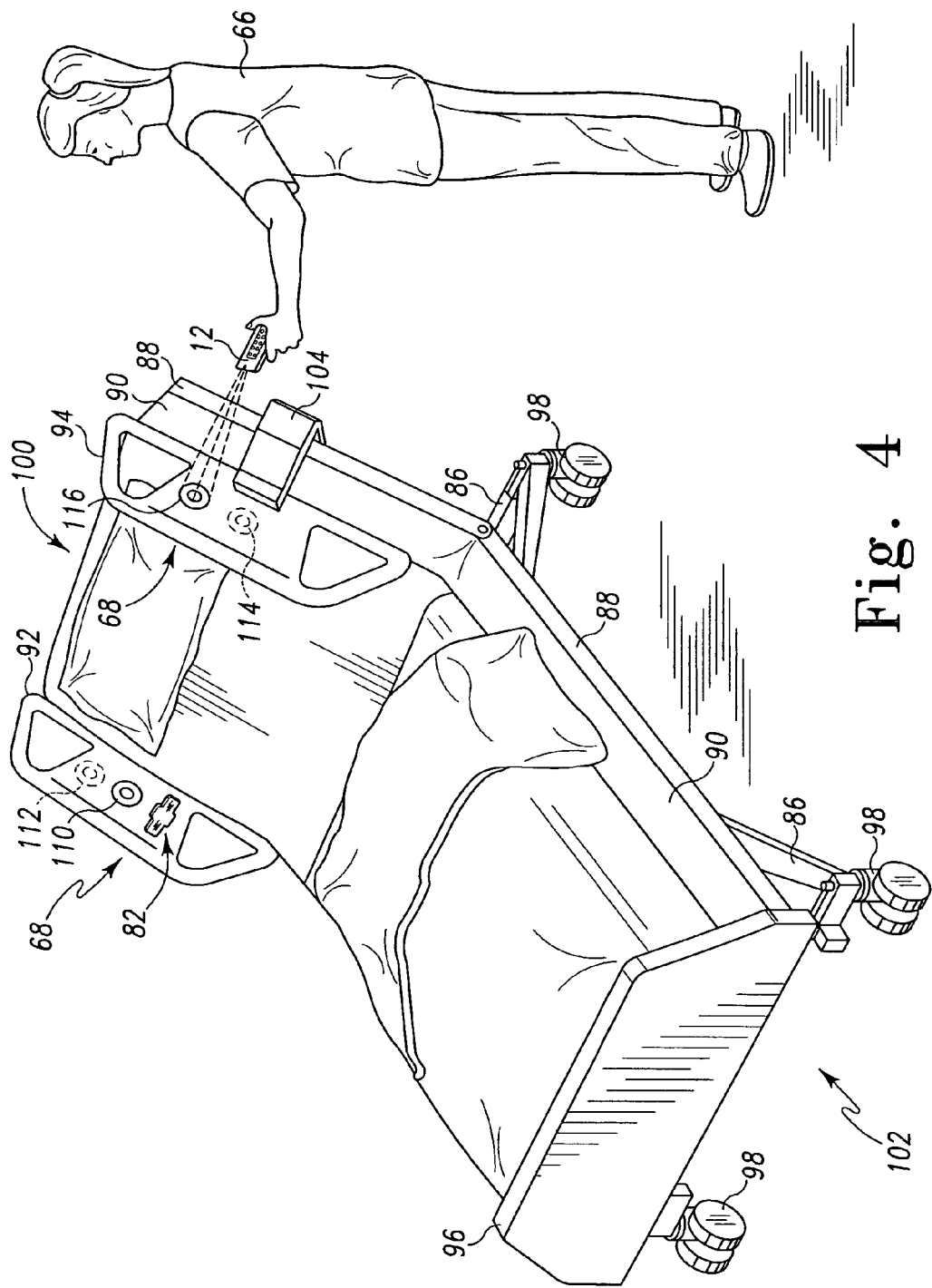
FIG. 4 is a perspective view showing a patient operating the wireless patient pendant of FIG. 2 to communicate with a second receiver located on one of the siderails of the bed of FIG. 3.
Figure 5:
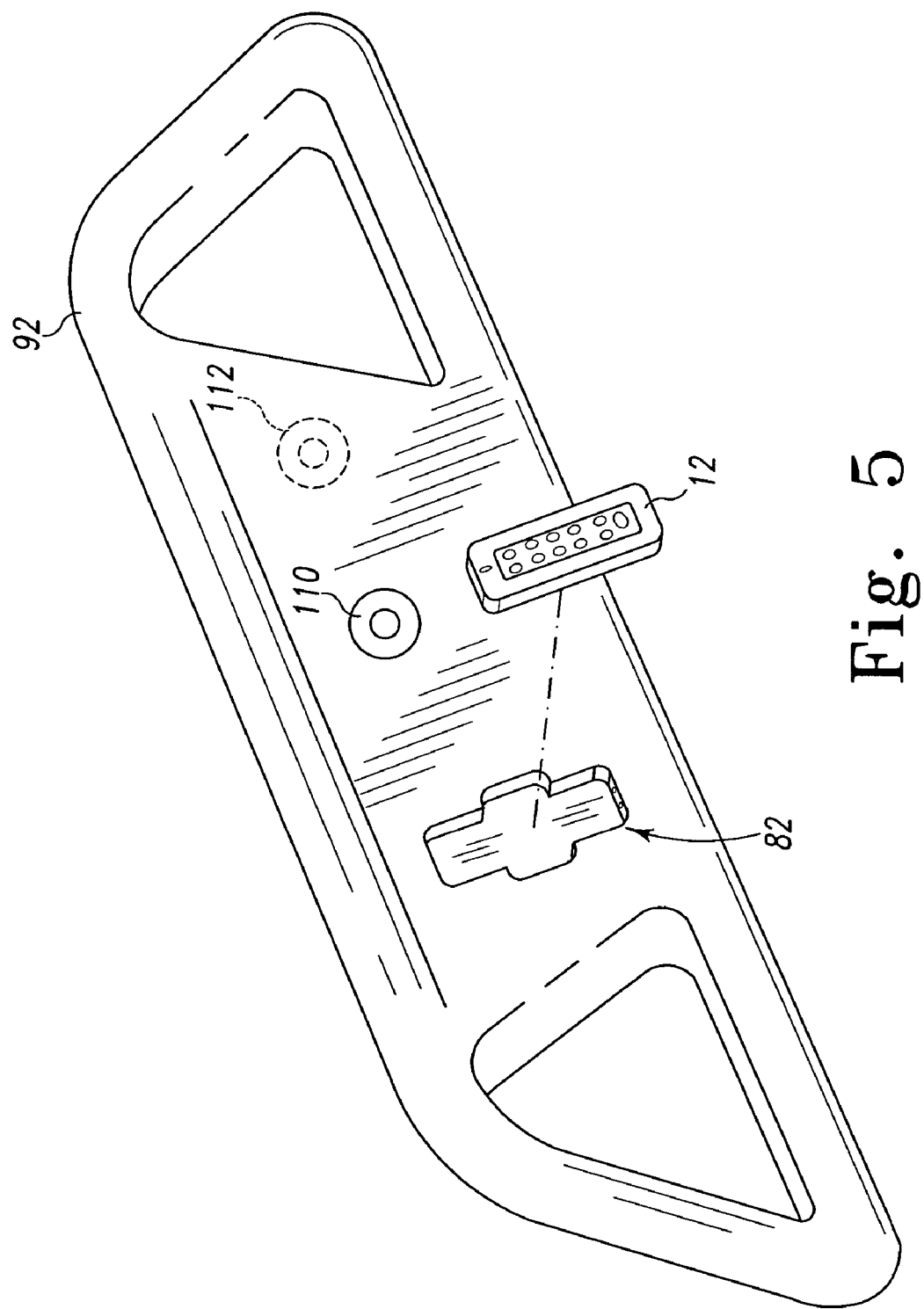
FIG. 5 is a perspective view of one of the siderails of the bed of FIG. 3 showing the pendant arranged for insertion into a recess in the siderail.

Referring now to FIGS. 3-5, the apparatus 14 also includes a frame 86, a patient-support deck 88 movably coupled to the frame 86, a mattress 90 positioned on the deck 88, a patient right siderail 92, and a patient left siderail 94. Additionally, the apparatus 14 may include other devices and features typically included in patient-support apparatuses. For example, as illustrated in FIG. 4, the apparatus 14 includes a foot board 96 and wheels 98 coupled to the frame 86 to facilitate the movement of the apparatus 14.

The patient-support deck 88 is controllably movable to one of a number of positions via the bed articulation system 74. For example, a head section 100 of the deck 88 may be inclined to elevate the upper body of a patient 66 resting on the mattress 90. Alternately, a foot section 102 of the deck 88 may be inclined to elevate the lower body of the patient 66. Additionally, the deck 88 may be movable to a Trendelenberg or reverse-Trendelenberg position.

The mattress 90 may be any type of mattress commonly used in patient-support apparatuses. For example, the mattress may be a spring mattress, air mattress, foam mattress, or any other type of mattress. Additionally, the mattress 90, deck 88, and/or frame 86 may include sensors and/or other electrical devices for monitoring the mattress 90 and/or the patient. The mattress 90 is positioned on deck 88 and supports the patient 66 resting thereon.

Each of the siderails 92, 94 is coupled to the frame 88 via a siderail support 104 which is configured to permit movement of the siderails 92, 94 between a raised position and a lowered position. The siderails 92, 94 may be moved to the lowered position to allow the patient 66 to exit the apparatus 14 or to the raised position when the patient 66 is resting on the apparatus 14 to protect the patient 66 from exiting the apparatus 14 undesirably.

As described above in regard to FIG. 1, the apparatus 14 includes one or more wireless receivers (e.g., transceivers) 68. For example, as illustrated in FIGS. 3-5, the illustrative apparatus 14 includes wireless receivers 110 and 112 located on the patient right siderail 92 and wireless receivers 114 and 116 located on the patient left siderail 94. The receivers 110, 112, 114, 116 may be dedicated wireless receivers or may form portions of one or more transceivers. The receivers 110 and 114 are located on a side of the siderails 92, 94, respectively, that faces generally toward the mattress 90 and the patient 66 when the patient 66 is resting on the apparatus 14 as illustrated in FIG. 3. However, the receivers 110 and 114 may be located in any position on the apparatus 14 that is wirelessly accessible by the patient 66 via the controller 12 when the patient 66 is resting on the apparatus 14 including, for example, the footboard 102 or a headboard (not shown). The receivers 112 and 116 are located on an opposite side of the siderails 92, 94, respectively, that faces generally away from the mattress 90. However, the receivers 112 and 116 may be located in any position on the apparatus 14 that is wirelessly accessible by the patient 66 via the controller 12 when the patient 66 is situated near the apparatus 14 (e.g., standing next to or sitting next to the apparatus 14)

In other embodiments, the apparatus 14 may include any number of receivers 68 positioned in any location on the apparatus 14 that is wirelessly accessibly by the patient 66. Further, as illustrated in FIGS. 3-5, the docking station 82 may be located on one or both of the siderails 92, 94 to accommodate storage of the controller 12 while the controller 12 is not in use by the patient 66. Alternatively, additional docking stations 82 may be located in any location accessible by the patient 66 while the patient is resting on the mattress 90 and/or by the patient 66 or a caregiver while the patient 66 or caregiver is standing or sitting near the apparatus 14.

In use, the patient 66 may operate the controller 12 to communicate with one of the receivers 110, 114 to control functions of the apparatus 14 and/or equipment 18 while resting on the mattress 90 as illustrated in FIG. 3. Alternatively, the patient 66 may operate the controller 12 to communicate with one of the receivers 112, 116 to control functions of the apparatus 14 and/or equipment 18 while standing or sitting near the apparatus 14 as illustrated in FIG. 4. Further, in some embodiments, the patient 66 may operate the controller 12 to communicate with a receiver of one of the hospital room equipment devices 18 to control functions of the equipment device 18. When the controller 12 is no longer needed by the patient 66, the patient 66 may store the controller 12 in the docking station 82. As discussed above in regard to FIG. 1, the docking station 82 may be configured to charge the controller 12 when the controller 12 is stored or otherwise positioned in the docking station 82.

Although certain embodiments have been described in detail above, variations and modifications exist within the scope and spirit of this disclosure as described and as defined in the following claims.

The invention claimed is:

1. A wireless control system for use with a patient-support apparatus, the wireless control system comprising:
   a first receiver located on a side rail of the patient-support apparatus;
   a second receiver (i) located apart from any patient-support apparatus and (ii) electrically connected to a hospital room equipment other than the patient-support apparatus; and
   a wireless hand-held controller for use by a patient, the wireless hand-held controller including:
      (i) a plurality of patient-support control inputs selectable by the patient to control functions of the patient-support apparatus;
      (ii) a plurality of hospital room equipment inputs different from the patient-support control inputs and selectable by the patient to control functions of the hospital room equipment;
      (iii) a first transmitter configured to transmit patient-support control signals directly to the first receiver to control functions of the patient-support apparatus in response to the patient selecting one of the plurality of patient-support control inputs, and
      (iv) a second transmitter configured to transmit hospital room equipment control signals directly to the second receiver to control functions of the hospital room equipment in response to the patient selecting one of the plurality of hospital room equipment inputs,
   wherein the communication range of the first transmitter and the first receiver is less than the communication range of the second transmitter and the second receiver.

2. The wireless control system of claim 1, wherein the first receiver is a portion of a transceiver configured to communicate with the wireless hand-held controller and with the second receiver.

3. The wireless control system of claim 1, wherein the first receiver is an infrared receiver.

4. The wireless control system of claim 1, wherein the second receiver is located on a wall of a hospital.

5. The wireless control system of claim 1, wherein the wireless hand-held controller is configured to communicate with the first and second receivers only while within a predetermined distance from a patient identification wristband.

6. The wireless control system of claim 1, wherein the wireless hand-held controller is configured to be received by a docking station of the patient-support apparatus.

7. The wireless control system of claim 6, wherein the wireless hand-held controller is inductively charged while received by the docking station.

8. The wireless control system of claim 1, wherein the hospital room equipment includes a patient station of a nurse call system.

9. The wireless control system of claim 1, wherein the hospital room equipment includes an environment control device.

10. The wireless control system of claim 1, wherein the hospital room equipment includes an entertainment device.

11. The wireless control system of claim 1, further comprising a third receiver located on the patient-support apparatus, wherein the first receiver is positioned to face generally toward a mattress of the patient-support apparatus and the third receiver is positioned to face generally away from the mattress.

* * * * *